(12) United States Patent
Li et al.

(10) Patent No.: US 9,243,086 B2
(45) Date of Patent: Jan. 26, 2016

(54) CATALYST COMPONENT FOR OLEFIN POLYMERIZATION AND CATALYST COMPRISING THE SAME

(75) Inventors: Weili Li, Beijing (CN); Xianzhi Xia, Beijing (CN); Yuexiang Liu, Beijing (CN); Jigui Zhang, Beijing (CN); Suzhen Qiao, Beijing (CN); Jin Zhao, Beijing (CN); Ping Gao, Beijing (CN); Xinsheng Wang, Beijing (CN); Yang Tan, Beijing (CN); Zhihui Zhang, Beijing (CN); Linna Yang, Beijing (CN); Ruilin Duan, Beijing (CN); Renqi Peng, Beijing (CN)

(73) Assignees: China Petroleum & Chemical Corporation, Beijing (CN); Beijing Research Inst. of Chemical Industry, China Petroleum & Chemical Corporation, Beijing (CN)

( * ) Notice: Subject to any disclaimer, the term of this patent is extended or adjusted under 35 U.S.C. 154(b) by 0 days.

(21) Appl. No.: 13/501,585

(22) PCT Filed: Oct. 18, 2010

(86) PCT No.: PCT/CN2010/001631
§ 371 (c)(1),
(2), (4) Date: Jun. 19, 2012

(87) PCT Pub. No.: WO2011/044760
PCT Pub. Date: Apr. 21, 2011

(65) Prior Publication Data
US 2012/0252992 A1    Oct. 4, 2012

(30) Foreign Application Priority Data

Oct. 16, 2009  (CN) ......................... 2009 1 0235562
Oct. 16, 2009  (CN) ......................... 2009 1 0235563
Oct. 16, 2009  (CN) ......................... 2009 1 0235564
Oct. 16, 2009  (CN) ......................... 2009 1 0235565

(51) Int. Cl.
| | | |
|---|---|---|
| C08F 4/649 | (2006.01) |
| C08F 110/06 | (2006.01) |
| C08F 4/654 | (2006.01) |
| C08F 10/00 | (2006.01) |
| C07F 3/00 | (2006.01) |

(52) U.S. Cl.
CPC ................. C08F 10/00 (2013.01); C07F 3/003 (2013.01); C08F 110/06 (2013.01)

(58) Field of Classification Search
USPC ....................................... 526/124.3
See application file for complete search history.

(56) References Cited

U.S. PATENT DOCUMENTS

| | | |
|---|---|---|
| 4,399,054 A | 8/1983 | Ferraris et al. |
| 4,421,674 A | 12/1983 | Invernizzi et al. |
| 4,469,648 A | 9/1984 | Ferraris et al. |
| 5,006,499 A | 4/1991 | Daire |
| 5,034,361 A | 7/1991 | Job et al. |
| 5,100,849 A | 3/1992 | Miya et al. |
| 5,817,591 A | 10/1998 | Shamshoum et al. |
| 5,849,655 A | 12/1998 | Shamshoum et al. |
| 6,020,279 A | 2/2000 | Uwai et al. |
| 6,127,304 A | 10/2000 | Sacchetti et al. |
| 6,323,152 B1 | 11/2001 | Sacchetti et al. |
| 6,617,278 B1 | 9/2003 | Jin et al. |
| 7,332,455 B2 | 2/2008 | Wei et al. |
| 7,388,061 B2 * | 6/2008 | Gao et al. ....................... 526/142 |
| 2004/0229748 A1 * | 11/2004 | Chen et al. .................... 502/118 |
| 2005/0239636 A1 | 10/2005 | Gao et al. |
| 2006/0287446 A1 | 12/2006 | Gao et al. |
| 2008/0167179 A1 | 7/2008 | Yang et al. |
| 2009/0182103 A1 | 7/2009 | Chang et al. |

FOREIGN PATENT DOCUMENTS

| | | |
|---|---|---|
| CN | 1016422 B | 4/1992 |
| CN | 1020448 C | 5/1993 |
| CN | 1141285 A | 1/1997 |
| CN | 1436796 A | 8/2003 |
| CN | 1453298 A | 11/2003 |
| CN | 1590415 A | 3/2005 |
| CN | 1611516 A | 5/2005 |

| | | |
|---|---|---|
| CN | 1611517 A | 5/2005 |
| CN | 1834118 A | 9/2006 |
| CN | 1922212 A | 2/2007 |
| CN | 1948352 A | 4/2007 |
| CN | 100348624 C | 11/2007 |
| CN | 101190953 A | 6/2008 |
| CN | 101421316 A | 4/2009 |
| EP | 0361493 A1 | 4/1990 |
| EP | 0395083 A2 | 10/1990 |
| EP | 0728724 A1 | 8/1996 |
| JP | 2002-506893 | 3/2002 |
| JP | 2005-517746 | 6/2005 |
| JP | 2006-523730 | 10/2006 |
| JP | 2007-505955 | 3/2007 |
| WO | WO 87/07620 | 12/1987 |
| WO | WO 93/11166 | 6/1993 |
| WO | WO 03/068723 | 8/2003 |
| WO | WO 03/068828 A1 | 8/2003 |
| WO | WO 2009/080568 A2 | 7/2009 |

OTHER PUBLICATIONS

International Search Report for International Patent Application No. PCT/CN2010/001631 mailed Jan. 20, 2011.
English language Abstract of CN 1948352A dated Apr. 18, 2007.
English language Abstract of CN 101190953A dated Jun. 4, 2008.
English language Abstract of CN 1453298A dated Nov. 5, 2003.
English language Abstract of CN 1590145A dated Mar. 9, 2005.
English language Abstract of CN 1611516A dated May 4, 2005.
English language Abstract of CN1611517A dated May 4, 2005.
English language Abstract of CN1834118A dated Sep. 20, 2006.

\* cited by examiner

*Primary Examiner* — Ling Choi
*Assistant Examiner* — Catherine S Branch

(74) *Attorney, Agent, or Firm* — Finnegan, Henderson, Farabow, Garrett & Dunner LLP

(57) ABSTRACT

A catalyst component for olefin polymerization is disclosed, which comprises a reaction product of the following components: (1) a spheric carrier; (2) a titanium compound; and optionally, (3) an electron donor, wherein the spheric carrier comprises a reaction product of at least the following components: (a) a magnesium halide represented by a general formula of $MgX_{2-n}R_n$, wherein X is independently chloride or bromide, R is a $C_1$-$C_{14}$ alkyl, a $C_6$-$C_{14}$ aryl, a $C_1$-$C_{14}$ alkoxy, or a $C_6$-$C_{14}$ aryloxy, and n is 0 or 1; (b) an alcohol compound; and (c) an epoxy compound represented by a general formula (I), wherein $R_2$ and $R_3$ are independently hydrogen, a $C_1$-$C_5$ linear or branched alkyl, or a $C_1$-$C_5$ linear or branched haloalkyl. When the catalyst of the invention is used in olefin polymerization, in particular in propylene polymerization, at least one of the following desired effects can be achieved: high polymerization activity of catalyst, high stereospecificity of catalyst, good hydrogen response of catalyst, high stereoregularity of polymer having high melt index, and low content of polymer fines.

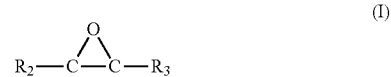

(I)

16 Claims, 3 Drawing Sheets

US 9,243,086 B2

CATALYST COMPONENT FOR OLEFIN POLYMERIZATION AND CATALYST COMPRISING THE SAME

CROSS REFERENCE OF RELATED APPLICATIONS

The present application claims the benefit of the Chinese Patent Application Nos. 200910235562.3, 200910235563.8, 200910235564.2 and CN200910235565.7, filed on Oct. 16, 2009, which are incorporated herein by reference in their entirety and for all purposes.

FIELD OF THE INVENTION

The present invention relates to a spheric catalyst component for olefin polymerization, a catalyst comprising the catalyst component, and use of the catalyst in the polymerization of olefin $CH_2=CHR$, wherein R is hydrogen or a $C_{1-12}$ alkyl, and more specifically, to a catalyst component obtainable by reacting a spheric magnesium-containing compound carrier with a titanium compound and an optional electron donor compound and use of the catalyst component.

BACKGROUND ART

Catalyst components comprising a titanium compound and an electron donor compound supported on an active magnesium halide carrier are well known in the art. A usual active magnesium halide carrier is an adduct of a magnesium halide and an alcohol, generally in the form of spheric particles. Spheric catalysts are obtained by reacting the magnesium halide-alcohol adduct carrier with a titanium compound, such as a titanium halide, and an electron donor compound. When used in olefin polymerization, in particular in propylene polymerization, such catalysts exhibit high polymerization activities and high stereospecificities, and the resulting polymers have good particle morphology.

The disclosed magnesium halide-alcohol adduct carriers comprise generally only magnesium dichloride and an alcohol. Some of the disclosed magnesium halide-alcohol adduct carriers further comprise a minor amount of water. Such magnesium halide-alcohol adduct carriers may be prepared by known processes, such as spray drying process, spray cooling process, high-pressure extruding process, or high speed stirring process. See, for example, U.S. Pat. No. 4,421, 674, U.S. Pat. No. 4,469,648, WO 08707620, WO 9311166, U.S. Pat. No. 5,100,849, U.S. Pat. No. 6,020,279, U.S. Pat. No. 4,399,054, EP0395083, U.S. Pat. No. 6,127,304, and U.S. Pat. No. 6,323,152.

Besides the above-mentioned magnesium halide-alcohol binary adduct carriers, the prior art also discloses other forms of active magnesium halide carriers. For example, CN1922212A discloses a carrier obtained by reacting a solution of a magnesium halide in a cyclic ether and an alcohol with a titanium halide. CN101190953A discloses a magnesium-containing adduct carrier formed by reacting a $C_1$-$C_5$ alcohol with powdery magnesium in the presence of a methyl halide. CN1590415A discloses a complex carrier prepared by reacting a $C_2$-$C_4$ lower alcohol with powdery magnesium in the presence of a methyl halide to form a homogeneous magnesium compound solution and supporting the formed magnesium compound on a spheric silica carrier. CN1016422B, U.S. Pat. No. 5,034,361, U.S. Pat. No. 5,849,655, U.S. Pat. No. 5,817,591 and U.S. Pat. No. 4,469,648 disclose active magnesium dichloride carriers prepared by using an alkoxy magnesium as a starting material.

SUMMARY OF THE INVENTION

After diligently studying, the inventors have found that a novel particulate magnesium compound can be obtained by reacting a magnesium halide-alcohol adduct solution with an epoxy compound. The particulate magnesium compound may be used as a carrier to react with a titanium compound and an optional internal electron donor, thereby providing a catalyst component for olefin polymerization. On this basis, the present invention was made.

An object of the invention is to provide a titanium-based spheric catalyst component supported on the novel magnesium compound carrier.

A further object of the invention is to provide a process for preparing the catalyst component according to the invention.

A still further object of the invention is to provide a catalyst for olefin polymerization, comprising a reaction product of the catalyst component, an alkyl aluminum compound as a cocatalyst and an optional external electron donor.

A still further object of the invention is to provide a process for polymerizing olefin(s), comprising contacting one olefin of formula $CH_2=CHR$, wherein R is hydrogen or a $C_{1-12}$ alkyl, and an optional comonomer with the catalyst of the invention under polymerization conditions, to form an olefin polymer; and recovering the resulting polymer.

The process for preparing the catalyst component of the invention is simple and feasible, and the resultant catalyst component has controllable particle morphology and particle size. When used in olefin polymerization, in particular in propylene polymerization, the catalyst of the invention achieves at least one of the following desired effects: high polymerization activity of catalyst, high stereospecificity of catalyst, good hydrogen response of catalyst, high stereoregularity of polymer having high melt index, and low content of polymer fines.

DETAILED DESCRIPTION OF THE PREFERRED EMBODIMENTS

Figure 1:
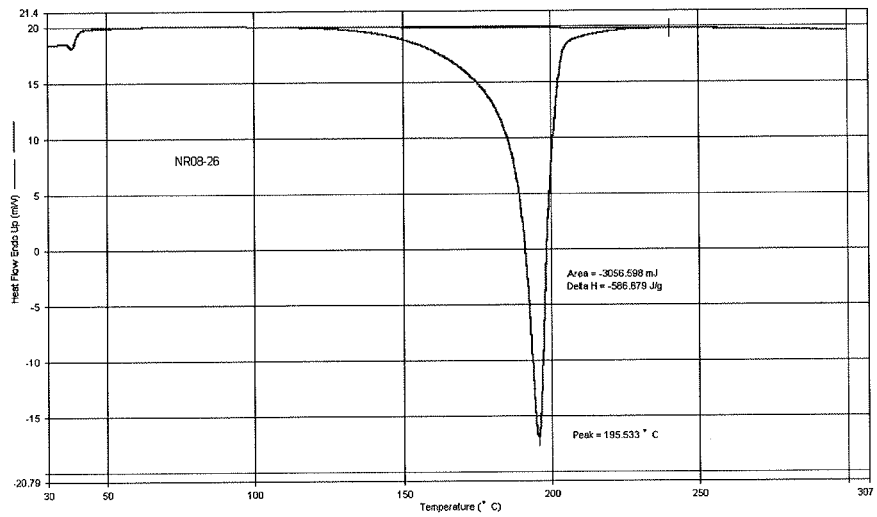
FIG. 1 shows a DSC curve of the carrier prepared in Example 1.

The term "polymerization" as used herein intends to include homopolymerization and copolymerization. The term "polymer" as used herein intends to include homopolymer, copolymer and terpolymer.

As used herein, the term "catalyst component" intends to mean main catalyst component or procatalyst, which, together with a conventional cocatalyst such as an alkyl aluminum compound and an optional external electron donor, constitutes the catalyst for olefin polymerization.

As used herein, the term "spheric carrier" means that the carrier has a spheroid-like particle morphology, but does not require that the particles of the carrier are in the form of perfect spheroid. Similarly, as used herein, the term "spheric catalyst component" or "spheric catalyst" means that the catalyst component or the catalyst has a spheroid-like particle morphology, but does not require that the particles of the catalyst component or the catalyst are in the form of perfect spheroid.

In a first aspect, the present invention provides a catalyst component for olefin polymerization, comprising a reaction product of:

(1) a spheric carrier;
(2) a titanium compound; and
(3) optionally, an electron donor, wherein the spheric carrier comprises a reaction product of at least the following components:

(a) a magnesium halide represented by a general formula of $MgX_{2-n}R_n$, wherein X is independently chloride or bromide, R is independently a $C_1$-$C_{14}$ alkyl, a $C_6$-$C_{14}$ aryl, a $C_1$-$C_{14}$ alkoxy, or a $C_6$-$C_{14}$ aryloxy, and n is 0 or 1;

(b) an alcohol compound, preferably an alcohol compound represented by a general formula of $R_1OH$, wherein $R_1$ is a $C_1$-$C_{12}$ alkyl, a $C_3$-$C_{10}$ cycloalkyl, a $C_7$-$C_{12}$ aralkyl or a $C_6$-$C_{10}$ aryl, and preferably a $C_1$-$C_8$ alkyl; and (c) an epoxy compound represented by a general formula (I):

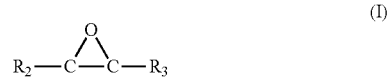

(I)

wherein $R_2$ and $R_3$ are independently hydrogen, a $C_1$-$C_5$ linear or branched alkyl, or a $C_1$-$C_5$ linear or branched haloalkyl, and preferably hydrogen, a $C_1$-$C_3$ alkyl or a $C_1$-$C_3$ haloalkyl.

The spheric carrier used in the preparation of the catalyst component of the invention may be prepared by a process comprising a) mixing the magnesium halide of the general formula of $MgX_{2-n}R_n$, the alcohol compound and an optional inert liquid medium in a vessel, preferably in a closed vessel, heating the resultant mixture to a temperature of from 30 to 160° C. and allowing it to react, to form a magnesium halide-alcohol adduct solution; and b) reacting the magnesium halide-alcohol adduct solution with the epoxy compound of the general formula (I):

(I)

at a temperature of from 30 to 160° C., to form the spheric carrier, wherein R, X, $R_2$ and $R_3$ are as defined above.

In the above process, relative to one mole of the magnesium halide, the amount of the alcohol used may ranges from 4 to 40 moles, preferably from 4 to 30 moles, more preferably from 6 to 25 moles, and still more preferably from 6 to 20 moles, and the amount of the epoxy compound used may ranges from 1 to 10 moles, and preferably from 2 to 6 moles.

Examples of the magnesium halide compound include, but are not limited to, magnesium dichloride, magnesium dibromide, phenoxy magnesium chloride, isopropoxy magnesium chloride, and butoxy magnesium chloride, with magnesium dichloride being preferred. The magnesium halides may be used alone or in combination.

The alcohol compound is preferably ones of the general formula of $R_1OH$, wherein $R_1$ is a $C_1$-$C_{12}$ alkyl, a $C_3$-$C_{10}$ cycloalkyl, a $C_7$-$C_{12}$ aralkyl or a $C_6$-$C_{10}$ aryl, and preferably a $C_1$-$C_8$ alkyl. The alcohol compound can also be glycols. Examples of the alcohol compound useful in the invention include, but are not limited to, methanol, ethanol, propanol, isopropanol, n-butanol, isobutanol, pentanol, isopentanol, n-hexanol, n-octanol, 2-ethylhexanol, ethylene glycol and propylene glycol. The alcohol compounds may be used alone or in combination.

Examples of the epoxy compound of the general formula (I) include, but are not limited to, epoxy ethane, epoxy propane, epoxy butane, epoxy chloropropane, epoxy chlorobutane, epoxy bromopropane, and epoxy bromobutane. The epoxy compounds may be used alone or in combination.

The inert liquid medium may be chosen from liquid aliphatic, aromatic or alicyclic hydrocarbons, silicone oils, and mixtures thereof. Examples include, but are not limited to, hexanes, heptanes, octanes, nonanes, decanes, dodecanes, kerosenes, paraffin oils, vaseline oils, white oils, methylsilicone oils, and mixtures thereof. If the inert liquid medium is used, there is not a specific limitation to the amount thereof. However, the inert liquid medium is preferably used in an amount of from ⅓ to 20 L, and preferably from ⅔ to 10 L, relative to one mole of the magnesium halide.

In the above process, a trace amount of water present in the magnesium halide and/or the alcohol can be involved in the reaction to form the magnesium halide-alcohol adduct solution.

In step a) of the above process, the individual materials may be added into the vessel in any order.

In an embodiment, the magnesium-containing spheric carrier may be prepared by a process comprising 1) preparing a magnesium halide-alcohol adduct solution by heating a mixture of the magnesium halide, the alcohol and the inert liquid medium in a closed vessel with stirring to a temperature of from 30 to 160° C., and preferably from 60 to 120° C., and allowing the mixture to react sufficiently; and 2) forming the particulate magnesium-containing spheric carrier by adding the epoxy compound into the magnesium halide-alcohol adduct solution while stirring and allowing the resultant mixture to react at a temperature of from 30 to 160° C., and preferably from 60 to 120° C.

In another embodiment, the magnesium-containing spheric carrier may be prepared by a process comprising 1) preparing a magnesium halide-alcohol adduct solution by heating a mixture of the magnesium halide, the alcohol and the inert liquid medium in a closed vessel with stirring to a temperature of from 30 to 160° C., and preferably from 60 to 120° C., and allowing the mixture to react sufficiently; and 2) forming the particulate magnesium-containing spheric carrier by adding the magnesium halide-alcohol adduct solution into a mixture of the epoxy compound and the inert liquid medium while stirring and allowing the resultant mixture to react at a temperature of from 30 to 160° C., and preferably from 60 to 120° C.

The total amount of the inert liquid medium used in steps 1) and 2) ranges from ⅓ to 20 L, and preferably from ⅔ to 10 L, relative to one mole of the magnesium halide. The inert liquid medium may be distributed at any suitable ratio between steps 1) and 2). For example, the ratio of the inert liquid medium used in step 1) to that used in step 2) may range from 1:10-5:1.

In another embodiment, the magnesium-containing spheric carrier may be prepared by a process comprising: reacting the magnesium halide with the alcohol in the inert liquid medium in a closed vessel at a temperature below 60° C. with stirring, to form a magnesium halide-alcohol adduct solution; adding the epoxy compound thereto; heating the resultant mixture with stirring to a temperature of from 60 to 160° C., and preferably from 60 to 120° C. and allowing the mixture to react sufficiently, to form the magnesium-containing spheric carrier particles. In this embodiment, the amount of the alcohol used ranges preferably from 10 to 30 moles, and more preferably from 15 to 25 moles, relative to one mole of the magnesium halide.

The DSC curves of the magnesium-containing spheric carriers of the invention have a distinct exothermal peak at a temperature range of from 70 to 250° C., said exothermal peak having a peak maximum at a temperature of from 100 to 220° C. and corresponding to an exothermal enthalpy of larger than 40 J/g. In an embodiment, the peak maximum appears at a temperature of from 100 to 200° C. In another embodiment, the peak maximum appears at a temperature of from 130 to 210° C. In another embodiment, the peak maximum appears at a temperature of from 130 to 200° C. In an embodiment, the exothermal peak corresponds to an exothermal enthalpy of larger than 100 J/g.

The X-ray diffraction patterns of the magnesium-containing spheric carriers of the invention have at least two diffraction lines at a 2θ angle range of from 5 to 15°, wherein the intensest diffraction line appears at a 2θ diffraction angle range of 10.0±0.4°, and the secondary intensest diffraction line appears at a 2θ diffraction angle range of from 10.5 to 12.5°, for example at a 2θ diffraction angle range of 11.5±0.4°, and has an intensity of at least 0.2 times of the intensity of the intensest diffraction line; and the X-ray diffraction patterns have a broad diffraction peak at a 2θ angle range of from 15 to 32° with a peak maximum at a 2θ angle range of from 20 to 21°, and at least one shoulder peak at a 2θ angle of 16.5±0.4° and/or 25.6±0.4°.

Without being limited to any specific theory, it is believed that the magnesium-containing spheric carriers of the invention prepared from the $MgX_2$, the $R_1OH$ and the epoxy compound of the formula (I) have a formula:

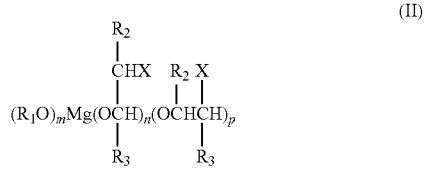

(II)

wherein p+m+n=2.

Taking a carrier prepared from magnesium dichloride, epoxy chloropropane, and ethanol as an example, it is possible that the magnesium compound is formed through the following reaction mechanism:

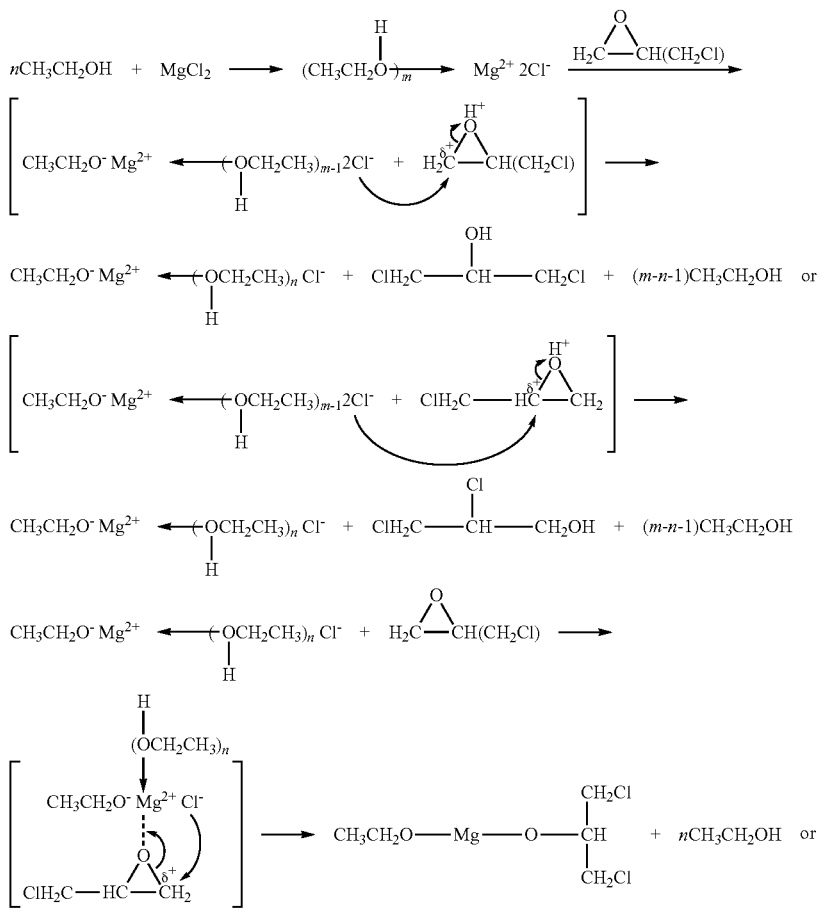

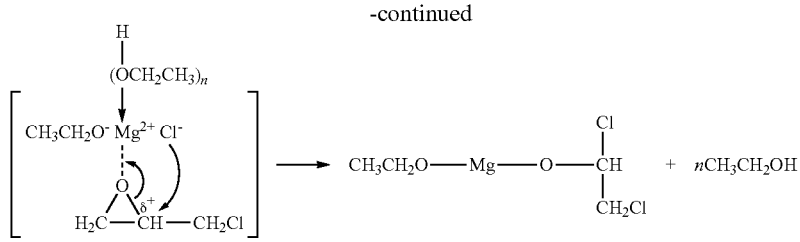

The titanium compound as the component (2) of the catalyst component according to the invention is especially preferably at least one represented by a formula of $Ti(OR^5)_{4-m}X_m$, wherein $R^5$ is a $C_1$-$C_{14}$ aliphatic hydrocarbyl, X is F, Cl, Br, I or a combination thereof, and m is an integer ranging from 1 to 4. Examples include, but are not limited to, titanium tetrachloride, titanium tetrabromide, titanium tetraiodide, tetrabutoxy titanium, tetraethoxy titanium, tributoxy titanium chloride, dibutoxy titanium dichloride, butoxy titanium trichloride, triethoxy titanium chloride, diethoxy titanium dichloride, ethoxy titanium trichloride, and mixtures thereof, with titanium tetrachloride being preferred. The titanium compound as the component (2) may also be titanium trichloride.

The internal electron donor as the optional component (3) of the catalyst component according to the invention may be chosen from the various compounds known in the art as being useful as internal electron donor, such as esters, ethers, ketones, amines and silanes. Preferably, the internal electron donor is chosen from esters of mono- and poly-carboxylic acids, esters of diol and ethers.

Preferred esters of mono- and poly-carboxylic acids include benzoates, phthalates, malonates, succinates, glutarates, pivalates, adipates, sebacates, maleates, naphthalene dicarboxylates, trimellitates, benzene-1,2,3-tricarboxylates, pyromellitates and carbonates. Examples include ethyl benzoate, diethyl phthalate, di-iso-butyl phthalate, di-n-butyl phthalate, di-iso-octyl phthalate, di-n-octyl phthalate, diethyl malonate, dibutyl malonate, diethyl 2,3-di-isopropylsuccinate, di-isobutyl 2,3-di-isopropylsuccinate, di-n-butyl 2,3-diisopropylsuccinate, dimethyl 2,3-di-isopropylsuccinate, di-iso-butyl 2,2-dimethylsuccinate, di-iso-butyl 2-ethyl-2-methylsuccinate, diethyl 2-ethyl-2-methylsuccinate, diethyl adipate, dibutyl adipate, diethyl sebacate, dibutyl sebacate, diethyl maleate, di-n-butyl maleate, diethyl naphthalene dicarboxylate, dibutyl naphthalene dicarboxylate, triethyl trimellitate, tributyl trimellitate, triethyl benzene-1,2,3-tricarboxylate, tributyl benzene-1,2,3-tricarboxylate, tetraethyl pyromellitate, tetrabutyl pyromellitate, etc.

Preferred ester compounds further include esters of polyols represented by the general formula (III),

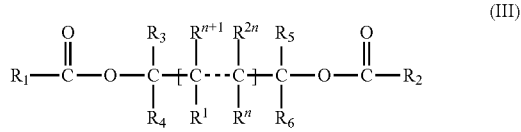

wherein $R_1$ to $R_6$ and $R^1$ to $R^{2n}$, which are identical or different, are hydrogen, halogen, or substituted or unsubstituted linear or branched $C_1$-$C_{20}$ alkyl, $C_3$-$C_{20}$ cycloalkyl, $C_6$-$C_{20}$ mono-ring or multi-ring aryl, $C_7$-$C_{20}$ alkylaryl, $C_7$-$C_{20}$ aralkyl, $C_2$-$C_{10}$ alkenyl, or $C_2$-$C_{10}$ ester group, with the proviso that $R_1$ and $R_2$ are not hydrogen; $R_3$ to $R_6$ and $R^1$ to $R^{2n}$ optionally comprise one or more heteroatoms, which are chosen from nitrogen, oxygen, sulfur, silicon, phosphorus and halogen, replacing carbon atom(s) or hydrogen atom(s) or the both; one or more of $R_3$ to $R_6$ and $R^1$ to $R^{2n}$ may be linked to form a ring; and n is an integer ranging from 0 to 10.

Preferred esters of diol are those represented by a general formula (IV):

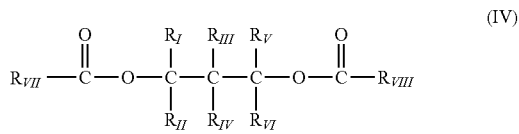

wherein $R_I$-$R_{VI}$, which are the same or different, represent hydrogen, a $C_1$-$C_{10}$ linear or branched alkyl, a $C_3$-$C_{10}$ cycloalkyl, a $C_6$-$C_{10}$ aryl, a $C_7$-$C_{101}$ alkaryl or a $C_7$-$C_{10}$ aralkyl; two or more groups of $R_I$-$R_{VI}$ may be linked to form one or more ring structures; $R_{VII}$ and $R_{VIII}$, which are the same or different, represent a $C_1$-$C_{10}$ linear or branched alkyl, a $C_3$-$C_{20}$ cycloalkyl, a $C_6$-$C_{20}$ aryl, a $C_7$-$C_{20}$ alkaryl or a $C_7$-$C_{20}$ aralkyl, wherein hydrogen atom(s) on the phenyl ring in the aryl, alkaryl or aralkyl is/are optionally replaced with halogen atom(s).

Among the esters of diol of the general formula (IV), the preferred are those wherein $R_I$, $R_{II}$, $R_V$ and $R_{VI}$ are not simultaneously hydrogen; the more preferred are those wherein at least one of $R_I$, $R_{II}$, $R_V$ and $R_{VI}$ is hydrogen; and the still more preferred are those wherein one of $R_I$ and $R_{II}$ is hydrogen and the other is methyl, ethyl, propyl, isopropyl, butyl, tert-butyl, phenyl or halophenyl; and one of $R_V$ and $R_{VI}$ is hydrogen and the other is methyl, ethyl, propyl, isopropyl, butyl, tert-butyl, phenyl or halophenyl.

Examples of suitable esters of diol include, but are not limited to, 1,3-propylene glycol dibenzoate, 2-methyl-1,3-propylene glycol dibenzoate, 2-ethyl-1,3-propylene glycol dibenzoate, 2,2-dimethyl-1,3-propylene glycol dibenzoate, (R)-1-phenyl-1,3-propylene glycol dibenzoate, 1,3-diphenyl-1,3-propylene glycol dibenzoate, 1,3-diphenyl-1,3-propylene glycol dipropionate, 2-methyl-1,3-diphenyl-1,3-propylene glycol dipropionate, 2-methyl-1,3-diphenyl-1,3-propylene glycol diacetate, 2,2-dimethyl-1,3-diphenyl-1,3-propylene glycol dibenzoate, 2,2-dimethyl-1,3-diphenyl-1,3-propylene glycol dipropionate, 1,3-di-tert-butyl-2-ethyl-1,3-propylene glycol dibenzoate, 1,3-diphenyl-1,3-propylene glycol diacetate, 1,3-diisopropyl-1,3-propylene glycol di-4-butylbenzoate, 2-amino-1-phenyl-1,3-propylene glycol dibenzoate, 2-methyl-1-phenyl-1,3-butylene glycol dibenzoate, phenyl-2-methyl-1,3-butylene glycol dipivalate, 3-butyl-2,4-pentylene glycol dibenzoate, 3,3-dimethyl-2,4-pentylene glycol dibenzoate, (2S,4S)-(+)-2,4-pentylene glycol dibenzoate, (2R,4R)-(+)-2,4-pentylene glycol dibenzoate, 2,4-pentylene glycol di-p-chlorobenzoate, 2,4-pentylene glycol di-m-chlorobenzoate, 2,4-pentylene glycol di-p-bromobenzoate, 2,4-pentylene glycol di-o-bromobenzoate, 2,4-pentylene glycol di-p-methylbenzoate, 2,4-pentylene glycol di-p-tert-butylbenzoate, 2,4-pentylene glycol di-p-butylbenzoate, 2-methyl-1,3-pentylene glycol di-p-chlorobenzoate, 2-methyl-1,3-pentylene glycol di-p-methylbenzoate, 2-butyl-1,3-pentylene glycol di-p-methylbenzoate, 2-methyl-1,3-pentylene glycol di-p-tert-butylbenzoate, 2-methyl-1,3-pentylene glycol pivalate, 2-methyl-1,3-pentylene glycol monobenzoate monocinnamate, 2,2-dimethyl-1,3-pentylene glycol dibenzoate, 2,2-dimethyl-1,3-pentylene glycol monobenzoate monocinnamate, 2-ethyl-1,3-pentylene glycol dibenzoate, 2-butyl-1,3-pentylene glycol dibenzoate, 2-allyl-1,3-pentylene glycol dibenzoate, 2-methyl-1,3-pentylene glycol dibenzoate, 2-ethyl-1,3-pentylene glycol dibenzoate, 2-propyl-1,3-pentylene glycol dibenzoate, 2-butyl-1,3-pentylene glycol dibenzoate, 2,2-dimethyl-1,3-pentylene glycol dibenzoate, 1,3-pentylene glycol di-p-chlorobenzoate, 1,3-pentylene glycol di-m-chlorobenzoate, 1,3-pentylene glycol di-p-bromobenzoate, 1,3-pentylene glycol di-o-bromobenzoate, 1,3-pentylene glycol di-p-methylbenzoate, 1,3-pentylene glycol di-p-tert-butylbenzoate, 1,3-pentylene glycol di-p-butylbenzoate, 1,3-pentylene glycol monobenzoate monocinnamate, 1,3-pentylene glycol dicinnamate, 1,3-pentylene glycol dipropionate, 2-methyl-1,3-pentylene glycol monobenzoate monocinnamate, 2,2-dimethyl-1,3-pentylene glycol dibenzoate, 2,2-dimethyl-1,3-pentylene glycol monobenzoate monocinnamate, 2-ethyl-1,3-pentylene glycol dibenzoate, 2-butyl-1,3-pentylene glycol dibenzoate, 2-allyl-1,3-pentylene glycol dibenzoate, 2-methyl-1,3-pentylene glycol monobenzoate monocinnamate, 2,2,4-trimethyl-1,3-pentylene glycol diisopropylformate, 1-trifluoromethyl-3-methyl-2,4-pentylene glycol dibenzoate, 2,4-pentylene glycol di-p-fluoromethylbenzoate, 2,4-pentylene glycol di-2-furancarboxylate, 2-methyl-6-ene-2,4-heptylene glycol dibenzoate, 3-methyl-6-ene-2,4-heptylene glycol dibenzoate, 4-methyl-6-ene-2,4-heptylene glycol dibenzoate, 5-methyl-6-ene-2,4-heptylene glycol dibenzoate, 6-methyl-6-ene-2,4-heptylene glycol dibenzoate, 3-ethyl-6-ene-2,4-heptylene glycol dibenzoate, 4-ethyl-6-ene-2,4-heptylene glycol dibenzoate, 5-ethyl-6-ene-2,4-heptylene glycol dibenzoate, 6-ethyl-6-ene-2,4-heptylene glycol dibenzoate, 3-propyl-6-ene-2,4-heptylene glycol dibenzoate, 4-propyl-6-ene-2,4-heptylene glycol dibenzoate, 5-propyl-6-ene-2,4-heptylene glycol dibenzoate, 6-propyl-6-ene-2,4-heptylene glycol dibenzoate, 3-butyl-6-ene-2,4-heptylene glycol dibenzoate, 4-butyl-6-ene-2,4-heptylene glycol dibenzoate, 5-butyl-6-ene-2,4-heptylene glycol dibenzoate, 6-butyl-6-ene-2,4-heptylene glycol dibenzoate, 3,5-dimethyl-6-ene-2,4-heptylene glycol dibenzoate, 3,5-diethyl-6-ene-2,4-heptylene glycol dibenzoate, 3,5-dipropyl-6-ene-2,4-heptylene glycol dibenzoate, 3,5-dibutyl-6-ene-2,4-heptylene glycol dibenzoate, 3,3-dimethyl-6-ene-2,4-heptylene glycol dibenzoate, 3,3-diethyl-6-ene-2,4-heptylene glycol dibenzoate, 3,3-dipropyl-6-ene-2,4-heptylene glycol dibenzoate, 3,3-dibutyl-6-ene-2,4-heptylene glycol dibenzoate, 3-ethyl-3,5-heptylene glycol dibenzoate, 4-ethyl-3,5-heptylene glycol dibenzoate, 5-ethyl-3,5-heptylene glycol dibenzoate, 3-propyl-3,5-heptylene glycol dibenzoate, 4-propyl-3,5-heptylene glycol dibenzoate, 3-butyl-3,5-heptylene glycol dibenzoate, 2,3-dimethyl-3,5-heptylene glycol dibenzoate, 2,4-dimethyl-3,5-heptylene glycol dibenzoate, 2,5-dimethyl-3,5-heptylene glycol dibenzoate, 2,6-dimethyl-3,5-heptylene glycol dibenzoate, 3,3-dimethyl-3,5-heptylene glycol dibenzoate, 4,4-dimethyl-3,5-heptylene glycol dibenzoate, 4,5-dimethyl-3,5-heptylene glycol dibenzoate, 4,6-dimethyl-3,5-heptylene glycol dibenzoate, 4,4-dimethyl-3,5-heptylene glycol dibenzoate, 6,6-dimethyl-3,5-heptylene glycol dibenzoate, 3-ethyl-2-methyl-3,5-heptylene glycol dibenzoate, 4-ethyl-2-methyl-3,5-heptylene glycol dibenzoate, 5-ethyl-2-methyl-3,5-heptylene glycol dibenzoate, 3-ethyl-3-methyl-3,5-heptylene glycol dibenzoate, 4-ethyl-3-methyl-3,5-heptylene glycol dibenzoate, 5-ethyl-3-methyl-3,5-heptylene glycol dibenzoate, 3-ethyl-4-methyl-3,5-heptylene glycol dibenzoate, 4-ethyl-4-methyl-3,5-heptylene glycol dibenzoate, 9,9-bis(benzoyloxymethyl)fluorene, 9,9-bis((m-methoxybenzoyloxy)methyl)fluorene, 9,9-bis((m-chlorobenzoyloxy)methyl)fluorene, 9,9-bis((p-chlorobenzoyloxy)methyl)fluorene, 9,9-bis(cinnoyloxymethyl)fluorene, 9-(benzoyloxymethyl)-9-(propionyloxymethyl)fluorene, 9,9-bis(propionyloxymethyl)fluorene, 9,9-bis(acryloyloxymethyl)fluorene, and 9,9-bis(pivalyloxymethyl)fluorene.

Such esters of diol are disclosed in Chinese patent application Nos. CN1453298A and CN1436796A, WO 03/068828A1 and WO 03/068723A1, relevant contents of which are incorporated herein by reference.

The ether compounds useful in the invention as internal electron donor include 1,3-diether compounds represented by a general formula (V):

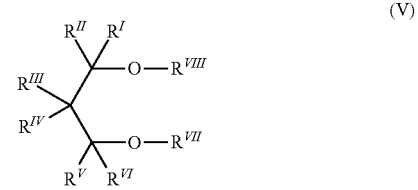

wherein $R^I$, $R^{II}$, $R^{III}$, $R^{IV}$, $R^V$ and $R^{VI}$, which are the same or different, are chosen from hydrogen, halogen, linear and branched $C_1$-$C_{20}$ alkyl, $C_3$-$C_{20}$ cycloalkyl, $C_6$-$C_{20}$ aryl, $C_7$-$C_{20}$ alkaryl, and $C_7$-$C_{20}$ aralkyl, and two of $R^1$ to $R^{VI}$ are optionally linked to form a ring; $R^{VII}$ and $R^{VIII}$, which are the same or different, are chosen from linear and branched $C_1$-$C_{20}$ alkyl, $C_3$-$C_{20}$ cycloalkyl, $C_6$-$C_{20}$ aryl, $C_7$-$C_{20}$ alkaryl and $C_7$-$C_{20}$ aralkyl.

Examples of 1,3-diether compound include, but are not limited to, 2-(2-ethylhexyl)-1,3-dimethoxypropane, 2-isopropyl-1,3-dimethoxypropane, 2-butyl-1,3-dimethoxypropane, 2-secbutyl-1,3-dimethoxypropane, 2-cyclohexyl-1,3-dimethoxypropane, 2-phenyl-1,3-dimethoxypropane, 2-(2-phenylethyl)-1,3-dimethoxypropane, 2-(2-cyclohexylethyl)-1,3-dimethoxypropane, 2-p-chlorophenyl-1,3-dimethoxypropane, 2-diphenylmethyl-1,3-dimethoxypropane, 2,2-dicyclohexyl-1,3-dimethoxypropane, 2,2-dicyclopentyl-1,3-dimethoxypropane, 2,2-diethyl-1,3-dimethoxypropane, 2,2-dipropyl-1,3-dimethoxypropane, 2,2-diisopropyl-1,3-dimethoxypropane, 2,2-dibutyl-1,3-dimethoxypropane, 2-methyl-2-propyl-1,3-dimethoxypropane, 2-methyl-2-benzyl-1,3-dimethoxypropane, 2-ethyl-2-methyl-1,3-dimethoxypropane, 2-methyl-2-isopropyl-1,3-dimethoxypropane, 2-methyl-2-phenyl-1,3-dimethoxypropane, 2-cyclohexyl-2-methyl-1,3-dimethoxypropane, 2,2-bis(2-cyclohexylethyl)-1,3-dimethoxypropane, 2-isobutyl-2-methyl-1,3-dimethoxypropane, 2-(2-ethylhexyl)-2-methyl-1,3-dimethoxypropane, 2,2-diisobutyl-1,3-dimethoxypropane, 2,2-diphenyl-1,3-dimethoxypropane, 2,2-dibenzyl-1,3-dimethoxypropane, 2,2-bis(cyclohexylmethyl)-1,3- dimethoxypropane, 2-isobutyl-2-isopropyl-1,3-dimethoxypropane, 2-(1-methylbutyl)-2-isopropyl-1,3-dimethoxypropane, 2-isopentyl-2-isopropyl-1,3-dimethoxypropane, 2-phenyl-2-isopropyl-1,3-dimethoxypropane, 2-sec-butyl-2-phenyl-1,3-dimethoxypropane, 2-benzyl-2-isopropyl-1,3-dimethoxypropane, 2-cyclopentyl-2-isopropyl-1,3-dimethoxypropane, 2-sec-butyl-2-cyclopentyl-1,3-dimethoxypropane, 2-cyclohexyl-2-isopropyl-1,3-dimethoxypropane, 2-sec-butyl-2-cyclohexyl-1,3-dimethoxypropane, 2-sec-butyl-2-isopropyl-1,3-dimethoxypropane, 2-cyclohexyl-2-cyclohexylmethyl-1,3-dimethoxypropane, and the like.

Such 1,3-diether compounds are disclosed in Chinese Patent No. CN1020448C, Chinese Patent No. CN100348624C, and Chinese Patent Application No. CN1141285A, relevant contents of which are incorporated herein by reference.

In a second aspect, the present invention provides a process for preparing the catalyst component of the invention, comprising: (1) providing the magnesium-containing spheric carrier according to the invention; (2) contacting the magnesium-containing spheric carrier with the titanium compound and the optional internal electron donor compound, to form the catalyst component; and (3) recovering the catalyst component.

In an embodiment, the catalyst component according to the invention is prepared by a process comprising the steps of: suspending the magnesium-containing spheric carrier in chilled titanium tetrachloride or a mixture of titanium tetrachloride and an inert solvent, with the temperature of the liquid being generally in a range of from −30° C. to 0° C., and preferably from −20° C. to −10° C.; heating the resulting mixture to a temperature of from 40° C. to 130° C., and preferably from 80° C. to 130° C., and maintaining at that temperature for 0.5 to 2.0 hours; then recovering the solids by filtration; optionally, repeating the above treatment with titanium tetrachloride one or more times, and preferably 1 to 4 times; and finally, washing the resultant solid catalyst component with an inert solvent several times, for example, 2 to 5 times. The inert solvent is preferably an aliphatic or aromatic hydrocarbon, such as hexane, heptane, octane, decane, toluene, and the like.

Before, during or after the reaction between the particulate magnesium-containing spheric carrier and the titanium compound, at least one internal electron donor compound may be used to treat the magnesium-containing spheric carrier. In particular, when the catalyst component is one intended to use in propylene polymerization, the addition of such an internal electron donor compound may be crucial in order to obtain a propylene polymer with a high isotacticity.

In the above process, relative to one mole of magnesium in the magnesium-containing spheric carrier, the amount of the internal electron donor compound used may range from 0 to 0.5 moles, and preferably from 0.05 to 0.3 moles; and the amount of the titanium compound used may range from 5 to 50 moles, and preferably from 8 to 30 moles.

In a third aspect, the present invention provides a catalyst for the polymerization of an olefin, comprising a reaction product of the following components:
a) the titanium-containing catalyst component according to the invention;
b) an alkylaluminum compound as a cocatalyst; and
c) optionally, an external electron donor compound.

Alkyl aluminum compounds useful as cocatalysts are well known to a person skilled in the art. The alkyl aluminum compounds are preferably those represented by a general formula of $AlR^a_{3-n}X_n$, wherein $R^a$ is independently hydrogen or a $C_1$-$C_{20}$ hydrocarbyl, and especially a $C_1$-$C_8$ alkyl; X is independently a halogen, and especially chloride; and n has a value ranging from 0 to 2. The alkyl aluminum compounds may be used alone or in combination. The preferred are $AlEt_3$, $Al(i-C_4H_9)_3$, $Al(n-C_4H_9)_3$, $Al(n-C_6H_{13})_3$, $Al(n-C_8H_{17})_3$, $AlEt_2Cl$, and the like. The alkyl aluminum compounds are generally used in such an amount that a molar ratio of aluminum therein to titanium in the component (1) ranges from 5 to 5000, preferably from 20 to 1000, and more preferably from 50 to 500.

The external electron donor may be any compound known in the art as being useful as an external electron donor. For example, the external electron donor may be a mono- or poly-carboxylic acid, a carboxylic anhydride, a carboxylic ester, a ketone, an ether, a lactone, an organophosphorus compound or an organic silicon compound, and preferably an organic silicon compound. The external electron donor may be used in an amount ranging from 0.005 to 0.5 moles per one mole of the alkyl aluminum compound, and preferably from 0.01 to 0.25 moles per one mole of the alkyl aluminum compound.

As the external electron donor, the preferred is silicon compounds of formula $R^1_x R^2_y Si(OR^3)_z$, wherein x and y are an integer ranging from 0 to 2, z is an integer ranging from 1 to 3, and the sum of (x+y+z) is 4; $R^1$, $R^2$ and $R^3$ are a $C_1$-$C_{18}$ hydrocarbyl, and preferably a $C_1$-$C_4$ linear or branched alkyl or a $C_5$-$C_6$ cycloalkyl, optionally containing heteroatom(s). Those silicon compounds wherein x is 1, y is 1, z is 2, at least one of $R^1$ and $R^2$ is a group chosen from branched alkyl, alkenyl, linear alkyl, cycloalkyl and aryl, having 3 to 10 carbon atoms and optionally containing heteroatom(s), and $R^3$ is a $C_1$-$C_{10}$ alkyl, especially methyl, are particularly preferred. Examples of preferred silicon compounds include, but are not limited to, cyclohexyl methyl dimethoxy silane, diisopropyl dimethoxy silane, di-n-butyl dimethoxy silane, di-isobutyl dimethoxy silane, diphenyl dimethoxy silane, methyl tert-butyl dimethoxy silane, dicyclopentyl dimethoxy silane, 2-ethylpiperidino tert-butyl dimethoxy silane, 1,1,1-trifluoro-2-propyl 2-ethylpiperidino dimethoxy silane and 1,1, 1-trifluoro-2-propyl methyl dimethoxy silane.

Preferred silicon compounds further include those wherein x is 0, z is 3, $R^2$ is a branched alkyl or cycloalkyl optionally containing heteroatom(s), and $R^3$ is methyl. Examples of such silicon compounds include cyclohexyl trimethoxy silane, tert-butyl trimethoxy silane and tert-hexyl trimethoxy silane.

The alkyl aluminum compound b) and the optional external electron donor compound c) can contact and react with the catalyst component a) separately or as a mixture.

The above catalyst is useful in the homopolymerization and copolymerization of olefin $CH_2$=CHR, wherein R is H or a $C_{1-12}$ alkyl.

Thus, in a fourth aspect, the present invention provides an olefin polymerization process, comprising contacting an olefin of formula $CH_2$=CHR, wherein R is hydrogen or a $C_{1-12}$ alkyl, and optionally a comonomer with the catalyst of the invention under polymerization conditions, to form an olefin polymer; and recovering the resulting polymer.

In a preferred embodiment, the olefin polymerization is homopolymerization of propylene or copolymerization of propylene and a comonomer. Examples of the comonomer copolymerizable with propylene include ethylene, $C_{4-12}$ alphaolefins, and $C_{5-20}$ diolefins.

The olefin polymerization may be carried out in liquid phase of liquid monomer or a solution of monomer in an inert solvent, or in gas phase, or in a combination of gas phase and liquid phase, according the known processes. Polymerization temperature is generally from 0° C. to 150° C., and preferably from 60° C. to 90° C., and polymerization pressure is a normal or higher pressure. In the polymerization, hydrogen as a regulator of polymer molecular weight may be added to the polymerization reactor to adjust the molecular weight of a polymer.

EXAMPLES

The following examples are provided to further illustrate the present invention and by no means intend to limit the scope thereof.
Testing Methods:
1. Melt index of polymers: measured according to ASTM D1238-99, at 230° C. and 2.16 kg load.
2. Isotacticity of polymers: measured by heptane extraction method carried out as follows: 2 g of dry polymer sample was extracted with boiling heptane in an extractor for 6 hours, then the residual substance was dried to constant weight, and the ratio of the weight of the residual polymer (g) to 2 (g) was regarded as isotacticity.
3. Particle size distribution: average particle size and particle size distribution of the particulate magnesium halide adducts were measured on Masters Sizer Model 2000 (manufactured by Malvern Instruments Co., Ltd.).
4. DSC curve: acquired on a DSC 7 instrument available from Perkin Elmer Co. by raising the temperature from 25 to 300° C. at a rate of 10° C./min under nitrogen atmosphere.
5. X-ray diffraction pattern: acquired on an X'Pert MPD Model multifunctional X-ray diffractometer with a graphite monochromator and a scintillation counter available from Philips Co., Netherlands, under the following conditions: CuKα (λ=1.5406 Å), tube voltage of 40 kV, tube current of 40 mA, DS=SS=1° slot system, receicing slot of 0.3 mm, scanning speed of 3° (2θ)/min., and scanning range of from 5° to 80° (2θ).

Example 1

Figure 2:
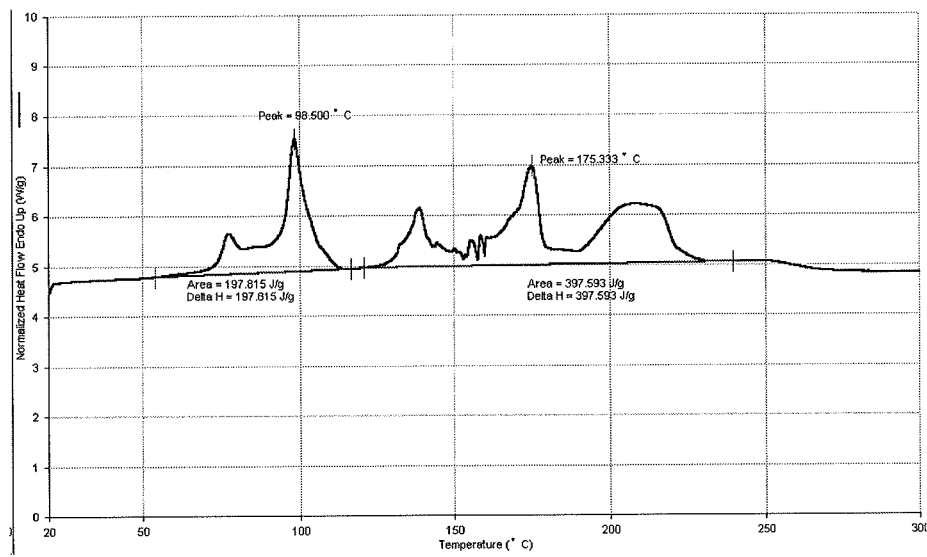
FIG. 2 shows a DSC curve of a known magnesium dichloride-ethanol adduct of formula $MgCl_2 \cdot 2.7C_2H_5OH$.
Figure 3:
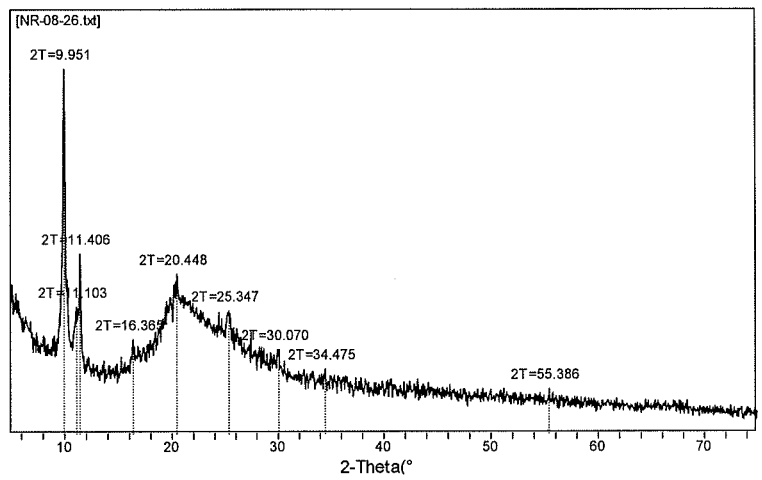
FIG. 3 shows an X-ray diffraction pattern of the carrier prepared in Example 1.
Figure 4:
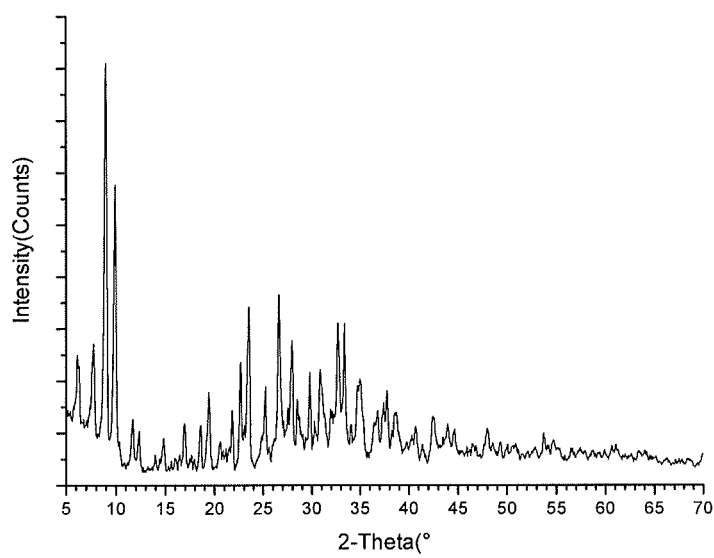
FIG. 4 shows an X-ray diffraction pattern of the known magnesium dichloride-ethanol adduct of formula $MgCl_2 \cdot 2.7C_2H_5OH$.
Figure 5:
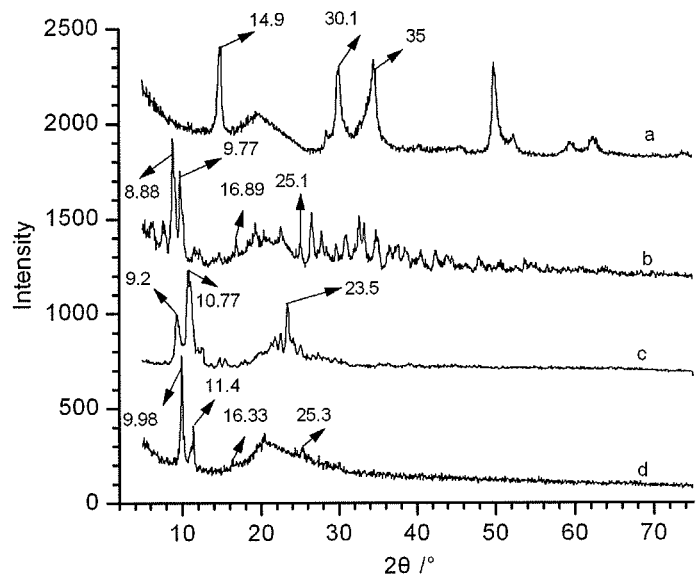
FIG. 5 shows X-ray diffraction patterns of several carriers, wherein a is one for $MgCl_2$; b is one for $MgCl_2 \cdot 2.7C_2H_5OH$; c is one for diethoxy magnesium; and d is one for the present carrier.
Figure 6:
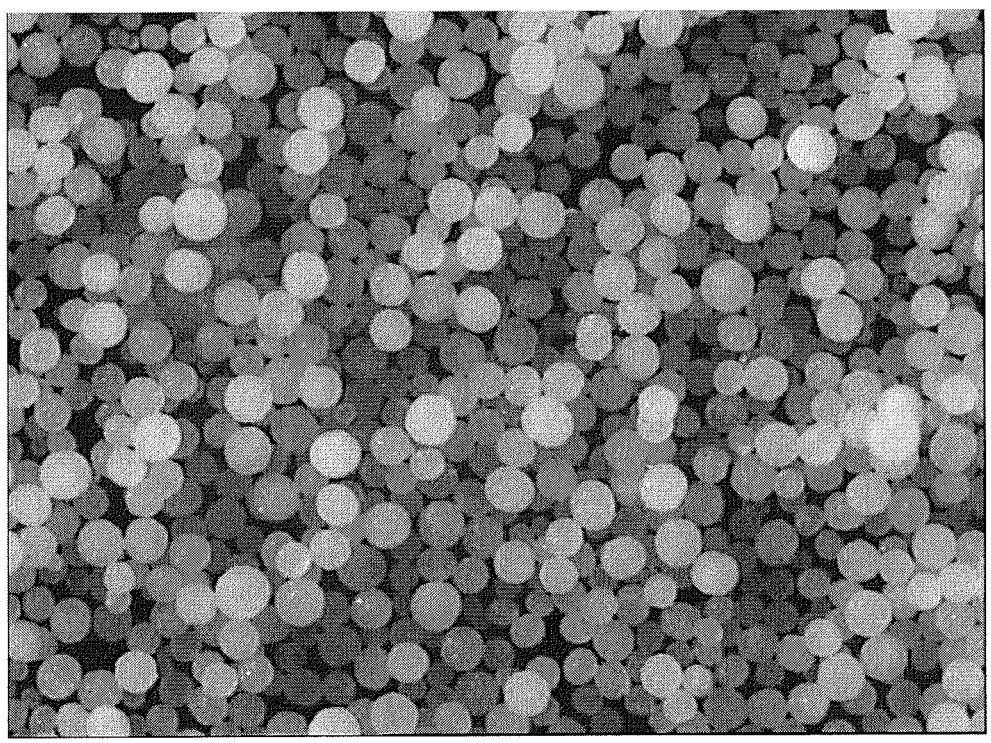
FIG. 6 shows a micrograph of the carrier prepared in Example 1.

A. Preparation of Spheric Magnesium-Containing Compound
To a 500 mL reactor were charged successively 7.2 g of magnesium dichloride, 180 ml of white oil and 82 ml of ethanol, and the contents were heated with stirring to 90° C. After the contents were allowed to react at that temperature for 1 hour, 24 ml of epoxy chloropropane was added to the reactor, and the reaction was allowed to continue at that temperature for 0.5 hours. After removing the liquid by filtration, the residual solids were washed with hexane five times and then dried under reduced pressure, to give a spheric magnesium-containing compound.
B. Preparation of Spheric Catalyst Component
100 ml of titanium tetrachloride was added to a 300 mL glass reactor and cooled to −20° C. Then 8 g of the above-prepared spheric magnesium compound was added to the reactor, and the contents were heated to 110° C., with 1.5 ml of diisobutyl phthalate (DIBP) being added to the reactor during the heating. After the liquid was removed through filtration, the residual solids were wished with titanium tetrachloride twice and with hexane thrice, and then dried under vacuum to give a spheric catalyst component.
C. Propylene Polymerization
A liquid phase bulk polymerization of propylene was conducted in a 5 L stainless steel autoclave as follows: under nitrogen atmosphere, to the autoclave were charged successively 2.5 L of propylene, 1 mmol of triethyl aluminum in 10 ml of hexane, 0.05 mmol of methyl cyclohexyl dimethoxy silane (CHMMS) in 1 ml of hexane, 10 mg of the above-prepared catalyst component and 1.5 L (standard volume) of hydrogen gas. The contents were heated to 70° C., and polymerization was allowed to continue at 70° C. for 1 hour. The autoclave was cooled and then the pressure was vented. The autoclave was opened and the resuling propylene polymer was recovered.
FIG. 1 shows a DSC curve of the carrier prepared in this Example, and FIG. 3 shows an X-ray diffraction pattern of this carrier. FIG. 2 shows a DSC curve of a known magnesium dichloride-ethanol adduct of formula $MgCl_2 \cdot 2.7C_2H_5OH$, and FIG. 4 shows an X-ray diffraction pattern of this magnesium dichloride-ethanol adduct. FIG. 5 further shows X-ray diffraction patterns of several carriers, wherein a is one for $MgCl_2$; b is one for $MgCl_2 \cdot 2.7C_2H_5OH$; c is one for diethoxy magnesium; and d is one for the present carrier. By comparing said DSC curves and X-ray diffraction patterns, it is apparent that the magnesium-containing carrier of the invention is different from the magnesium dichloride-ethanol adduct carrier and the magnesium dichloride carrier known in the art.

Example 2

100 ml of titanium tetrachloride was added to a 300 mL glass reactor and cooled to −20° C. Then 8 g of spheric carrier prepared according to step A of Example I was added to the reactor, and the contents were heated to 110° C. and maintained at that temperature for 0.5 hours. After filtering off the liquid, 80 ml of titanium tetrachloride and 1.5 ml of diisobutyl phthalate (DIBP) were added to the reactor, and the contents were heated to 120° C. After reacting for 0.5 hours, the liquid was removed through filtration, and the residual solids were wished with titanium tetrachloride twice and with hexane thrice, and then dried under vacuum to give a spheric catalyst component.
Propylene polymerization was conducted according to the procedure described in Example 1.

Example 3

A catalyst component was prepared according to the procedure described in Example 2. Propylene polymerization was conducted according to the procedure described in Example 1, except that the amount of hydrogen gas was changed to 3.0 L (standard volume).

Example 4

A catalyst component was prepared according to the procedure described in Example 2. Propylene polymerization was conducted according to the procedure described in Example 1, except that the amount of hydrogen gas was changed to 5.0 L (standard volume).

Example 5

A catalyst component was prepared according to the procedure described in Example 2. Propylene polymerization was conducted according to the procedure described in Example 1, except that the amount of hydrogen gas was changed to 8.0 L (standard volume).

Example 6

A catalyst component was prepared according to the procedure described in Example 2, except that the diisobutyl phthalate as internal electron donor was replaced with 2.0 ml of 2,4-pentylene glycol dibenzoate (PDB). Propylene polymerization was conducted according to the procedure described in Example 1.

Example 7

A catalyst component was prepared according to the procedure described in Example 2, except that the diisobutyl phthalate as internal electron donor was replaced with 2.0 ml of 2-isopentyl-2-isopropyl-1,3-dimethoxypropane (PPDE). Propylene polymerization was conducted according to the procedure described in Example 1.

Propylene polymerization was conducted according to the procedure described in Example 1.

Example 9

A catalyst component was prepared according to the procedure described in Example 8. Propylene polymerization was conducted according to the procedure described in Example 1, except that the amount of hydrogen gas was changed to 5.0 L (standard volume).

TABLE 1

Catalyst components and propylene polymerization results

| No. | Internal electron donor | Amount of hydrogen gas (L) | Polymerization activity (KgPP/gCat) | Isotacticity (%) | Polymer melt index (g/10 min) | Content of polymer fines* wt % |
|---|---|---|---|---|---|---|
| Example 1 | DIBP | 1.5 | 37.8 | 97.3 | 12 | 0.01 |
| Example 2 | DIBP | 1.5 | 32.6 | 97.7 | 7.8 | 0.05 |
| Example 3 | DIBP | 3.0 | 45.8 | 97.6 | 11.5 | 0.25 |
| Example 4 | DIBP | 5.0 | 41.3 | 97.5 | 30 | 0.27 |
| Example 5 | DIBP | 8.0 | 46.0 | 96.5 | 58 | 0.22 |
| Example 6 | PDB | 1.5 | 43.6 | 96.5 | 2.6 | 0.1 |
| Example 7 | PPDE | 1.5 | 49.7 | 98.0 | 9.8 | 0.31 |

*Polymer fines refer to those polymer particles having a particle size of less than 180 microns.

Table 1 shows the polymerization results of the catalysts obtained in Examples 1 to 7 when used in propylene polymerization. It can be seen from the data shown in Table 1 that the catalysts of the invention exhibit high polymerization activities and high stereospecificities, and the resulting polymers have low contents of polymer fines. Additionally, the catalysts have good hydrogen response. Particularly, even when the polymers obtained have high melt indices, they still have high isotacticities.

Example 10

A catalyst component was prepared according to the procedure described in Example 8. Propylene polymerization was conducted according to the procedure described in Example 1, except that the amount of hydrogen gas was changed to 8.0 L (standard volume).

TABLE 2

Catalyst components and propylene polymerization results

| No. | Internal electron donor | Amount of hydrogen gas (L) | Polymerization activity (KgPP/gCat) | Isotacticity (%) | Polymer melt index (g/10 min) | Content of polymer fines wt % |
|---|---|---|---|---|---|---|
| Example 8 | PDB + DIBP | 1.5 | 40.1 | 98.7 | 3.4 | 0.1 |
| Example 9 | PDB + DIBP | 5 | 44.3 | 97.0 | 24.4 | 0.15 |
| Example 10 | PDB + DIBP | 8 | 36.6 | 96.5 | 48.6 | 0.16 |

Example 8

100 ml of titanium tetrachloride was added to a 300 mL glass reactor and cooled to −20° C. Then 8 g of spheric magnesium compound prepared according to step A of Example 1 was added to the reactor, and the contents were heated to 110° C., with 1.0 ml of 2,4-pentylene glycol dibenzoate (PDB) and 0.5 ml of diisobutyl phthalate (DIBP) being added to the reactor during the heating. After the liquid was removed through filtration, the residual solids were wished with titanium tetrachloride twice and with hexane thrice, and then dried under vacuum to give a spheric catalyst component.

The patents, patent applications and testing methods cited in the specification are incorporated herein by reference.

While the invention has been described with reference to exemplary embodiments, it will be understood by those skilled in the art that various changes and modifications may be made without departing from the spirit and scope of the invention. Therefore, the invention is not limited to the particular embodiments disclosed as the best mode contemplated for carrying out this invention, but the invention will include all embodiments falling within the scope of the appended claims.

What is claimed is:

1. A catalyst component for olefin polymerization, comprising a reaction product of:

(1) a spherical carrier;
(2) a titanium compound; and
optionally, (3) an electron donor,
wherein the spherical carrier comprises solid particles directly formed in reaction of at least the following components:
(a) a magnesium halide represented by a general formula of $MgX_{2-n}R_n$, wherein X is independently chloride or bromide, R is a $C_1$-$C_{14}$ alkyl, a $C_6$-$C_{14}$ aryl, a $C_1$-$C_{14}$ alkoxy, or a $C_6$-$C_{14}$ aryloxy, and n is 0 or 1;
(b) an alcohol compound; and
(c) an epoxy compound represented by a general formula (I):

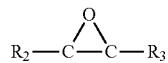

wherein $R_2$ and $R_3$ are independently hydrogen, a $C_1$-$C_5$ linear or branched alkyl, or a $C_1$-$C_5$ linear or branched haloalkyl.

2. The catalyst component of claim 1, wherein the alcohol compound is represented by a general formula of $R_1OH$, wherein $R_1$ is a $C_1$-$C_{12}$ alkyl, a $C_3$-$C_{10}$ cycloalkyl, a $C_7$-$C_{12}$ aralkyl or a $C_6$-$C_{10}$ aryl.

3. The catalyst component of claim 1, wherein the magnesium halide is magnesium dichloride.

4. The catalyst component of claim 2, wherein $R_1$ is a $C_1$-$C_8$ alkyl.

5. The catalyst component of claim 1, wherein $R_2$ and $R_3$, which are the same or different, represent hydrogen, a $C_1$-$C_3$ alkyl or a $C_1$-$C_3$ haloalkyl.

6. The catalyst component of claim 1, wherein an X-ray diffraction pattern of the spherical carrier has at least two diffraction lines at a 2θ angle range of from 5 to 15°, wherein the intensest diffraction line appears at a 2θ diffraction angle range of 10.0±0.4°, and the secondary intensest diffraction line appears at a 2θ diffraction angle range of from 10.5 to 12.5°, and has an intensity of at least 0.2 times of the intensity of the intensest diffraction line; and the X-ray diffraction pattern has a broad diffraction peak at a 2θ angle range of from 15 to 32° with a peak maximum at a 2θ angle range of from 20 to 21°, and at least one shoulder peak at a 2θ angle of 16.5±0.4° and/or 25.6±0.4°.

7. The catalyst component of claim 1, wherein a DSC curve of the spherical carrier has a distinct exothermal peak at a temperature range of from 70 to 250° C., said exothermal peak having a peak maximum at a temperature of from 100 to 220° C. and corresponding to an exothermal enthalpy of larger than 40 J/g.

8. The catalyst component of claim 1, wherein the titanium compound has a general formula of $Ti(OR^5)_{4-m}X_m$, wherein $R^5$ is a $C_1$-$C_{14}$ aliphatic hydrocarbyl, X is F, Cl, Br or I, and m is an integer ranging from 1 to 4.

9. The catalyst component of claim 1, wherein the electron donor is at least one chosen from esters of mono- and poly-carboxylic acids, esters of diol and 1,3-diethers.

10. The catalyst component of claim 9, wherein the esters of mono- and poly-carboxylic acids are benzoates, phthalates, malonates, succinates, glutarates, pivalates, adipates, sebacates, maleates, naphthalene dicarboxylates, trimellitates, benzene-1,2,3-tricarboxylates, and pyromellitates.

11. The catalyst component of claim 9, wherein the esters of diol are represented by a general formula (IV):

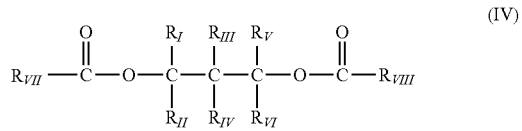

wherein $R_I$-$R_{VI}$, which are the same or different, represent hydrogen, a $C_1$-$C_{10}$ linear or branched alkyl, a $C_3$-$C_{10}$ cycloalkyl, a $C_6$-$C_{10}$ aryl, a $C_7$-$C_{10}$ alkaryl or a $C_7$-$C_{10}$ aralkyl; two or more groups of $R_I$-$R_{VI}$ may be linked to form one or more ring structures; $R_{VII}$ and $R_{VIII}$, which are the same or different, represent a $C_1$-$C_{10}$ linear or branched alkyl, a $C_3$-$C_{20}$ cycloalkyl, a $C_6$-$C_{20}$ aryl, a $C_7$-$C_{20}$ alkaryl or a $C_7$-$C_{20}$ aralkyl, wherein hydrogen atom(s) on the phenyl ring in the aryl, alkaryl or aralkyl may be optionally replaced with halogen atom(s).

12. The catalyst component of claim 11, wherein in the general formula (IV), $R_I$, $R_{II}$, $R_V$ and $R_{VI}$ are not simultaneously hydrogen.

13. The catalyst component of claim 11, wherein in the general formula (IV), one of $R_I$ and $R_{II}$ is hydrogen and the other is methyl, ethyl, propyl, isopropyl, butyl, tert-butyl, phenyl or halophenyl; and one of $R_V$ and $R_{VI}$ is hydrogen and the other is methyl, ethyl, propyl, isopropyl, butyl, tert-butyl, phenyl or halophenyl.

14. A catalyst for the polymerization of an olefin of formula $CH_2$=$CHR$, wherein R is hydrogen or a $C_{1-12}$ alkyl, comprising a reaction product of:
(1) the catalyst component of claim 1;
(2) an alkyl aluminum compound; and
(3) optionally, an external electron donor component.

15. The catalyst of claim 14, having at least one of the following features:
the alkyl aluminum compound is at least one represented by a general formula of $AlR^a_{3-n}X_n$, wherein $R^a$ is independently hydrogen or a $C_1$-$C_{20}$ hydrocarbyl, and especially a $C_1$-$C_8$ alkyl; X is independently a halogen, and especially chloride; and n has a value ranging from 0 to 2;
the alkyl aluminum compound is used in such an amount that a molar ratio of aluminum therein to titanium in the catalyst component (1) ranges from 5 to 5000, preferably from 20 to 1000, and more preferably from 50 to 500;
the external electron donor compound is chosen from carboxylic anhydrides, carboxylic esters, ketones, ethers, lactones, organophosphorus compounds, and organic silicon compounds of formula $R^1_xR^2_ySi(OR^3)_z$, wherein x and y are independently an integer ranging from 0 to 2, z is an integer ranging from 1 to 3, and the sum of (x+y+z) is 4; $R^1$, $R^2$ and $R^3$ are independently a $C_1$-$C_{18}$ hydrocarbyl, and preferably a $C_1$-$C_4$ linear or branched alkyl or a $C_5$-$C_6$ cycloalkyl, optionally containing heteroatom(s);
the external electron donor compound is used in an amount ranging from 0.005 to 0.5 moles per one mole of the alkyl aluminum compound, and preferably from 0.01 to 0.25 moles per one mole of the alkyl aluminum compound; and
the alkyl aluminum compound (2) and the optional external electron donor compound (3) contact and react with the catalyst component (1) separately or as a mixture.

16. A process for polymerizing olefin(s), comprising contacting an olefin of formula $CH_2$=$CHR$, wherein R is hydrogen or a $C_{1-12}$ alkyl, and an optional comonomer with the catalyst of claim 14 under polymerization conditions, to form an olefin polymer; and recovering the resulting polymer.

* * * * *